United States Patent [19]

Akhavi

[11] 4,367,754

[45] Jan. 11, 1983

[54] METHOD OF DISPENSING A BLOOD SAMPLE

[75] Inventor: David S. Akhavi, Los Angeles, Calif.

[73] Assignee: American Hospital Supply Corporation, Evanston, Ill.

[21] Appl. No.: 220,571

[22] Filed: Dec. 29, 1980

Related U.S. Application Data

[62] Division of Ser. No. 25,979, Apr. 2, 1979, Pat. No. 4,266,558.

[51] Int. Cl.³ .................. A61B 5/14; B65D 35/28; G01N 1/10
[52] U.S. Cl. .................................. 128/763; 128/767; 73/864.11; 222/102
[58] Field of Search .......................... 128/760–771, 128/346; 73/864.02, 864.11; 222/95, 102, 103

[56] References Cited

U.S. PATENT DOCUMENTS

| 917,442 | 4/1909 | Hutchinson | 73/864.11 X |
| 2,083,603 | 6/1937 | Hardwick | 222/95 |
| 2,965,255 | 12/1960 | Gerarde | 73/864.02 X |
| 3,768,978 | 10/1973 | Grubb et al. | 73/864.02 X |
| 4,164,223 | 8/1979 | Munib | 128/346 |
| 4,195,526 | 4/1980 | Amos et al. | 73/864.11 |
| 4,256,437 | 3/1981 | Brown | 128/214 F |

Primary Examiner—Kyle L. Howell
Assistant Examiner—John C. Hanley
Attorney, Agent, or Firm—Roger A. Williams

[57] ABSTRACT

A method of dispensing a blood sample from a flexible tube by pinching the tube with a clamp and stripping the blood from the tube by moving the clamp along the tube while the clamp is in a clamped position.

1 Claim, 6 Drawing Figures

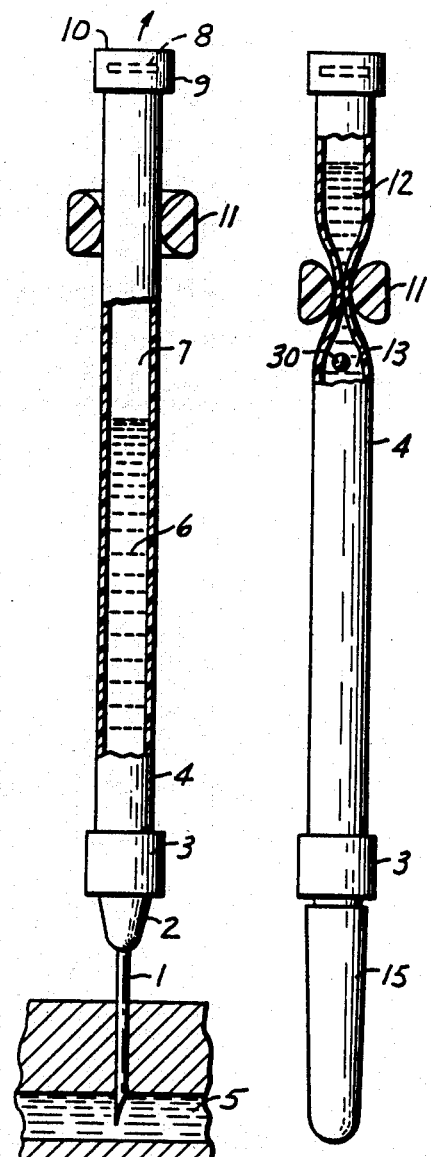
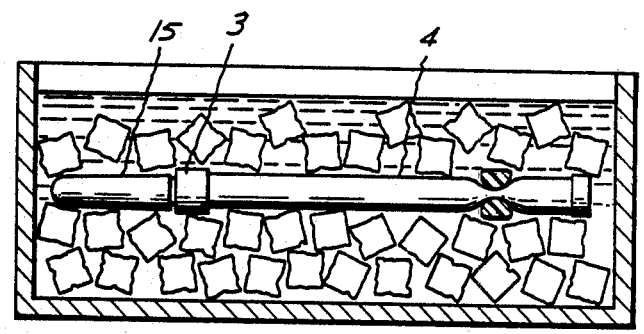
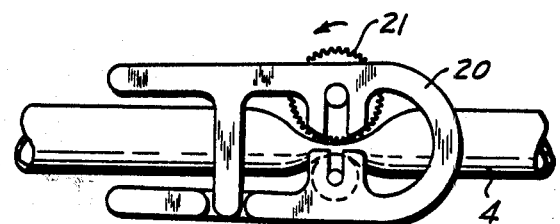
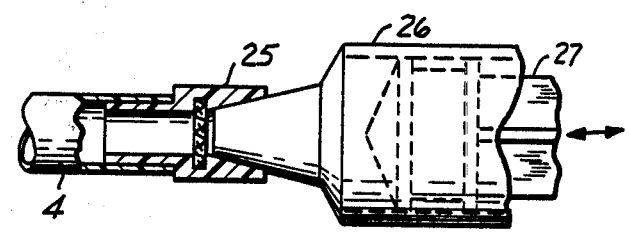
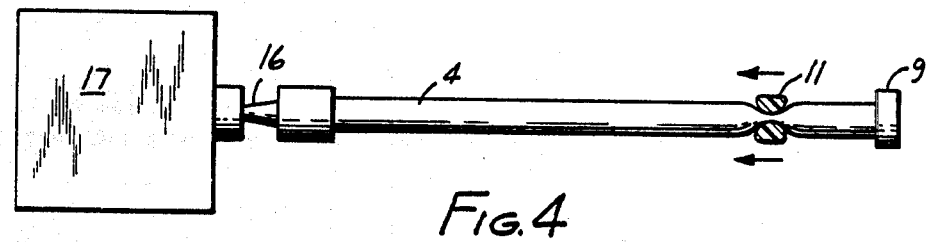

METHOD OF DISPENSING A BLOOD SAMPLE

This application is a division of application Ser. No. 025,979, filed Apr. 2, 1979, now U.S. Pat. No. 4,266,558, issued May 12, 1981.

BACKGROUND

There have been many problems with collecting blood samples, such as from an artery, so that there is minimal error in tests for partial pressures of oxygen and carbon dioxide in the blood sample. There has also been some problems in clearly distinguishing between arterial and venous blood when collecting the sample.

In my co-pending application entitled "Blood Sampler," Ser. No. 25,980, filed Apr. 2, 1979, now U.S. Pat. No. 4,266,559, issued May 12, 1981, I describe a unique flexible tube blood collector which has specific advantages for collecting arterial blood. The present application deals with the unique method of collecting blood with such a blood sampler.

A related co-pending application entitled "Stripper Clamp," invented by David S. Akhavi, Ser. No. 26,117, filed Apr. 2, 1979, now U.S. Pat. No. 4,266,751, issued May 12, 1981, relates to the specific structure of a clamp used in the method of collecting and dispensing a blood sample according to the present method.

SUMMARY OF THE INVENTION

The present invention relates to a method of collecting a blood sample, such as from an artery, in a flexible tube reservoir. In particular, the invention relates to a method of dispensing a blood sample from such a flexible tube reservoir by pinching the tube with a clamp and stripping the blood from the flexible tube reservoir by moving the clamp along the tube while the clamp is in its clamped position. The flexible tube is pinched off by means of a clamp to segment an air contaminated portion of the blood sample from a test portion of the blood sample. If a test is not immediately performed on the blood, it is chilled to prevent blood from continuing to metabolize oxygen and cause an erroneous test. The test portion of the blood sample is dispensed to a testing machine. If such machine does not have a vacuum extractor, blood is dispensed by pinchingly stripping the flexible tube with a sliding or rolling clamp structure.

THE DRAWINGS

FIG. 1 is a front elevational view of a blood sampler in the process of collecting a blood sample;

FIG. 2 is a front elevational view of the blood sampler after the blood has been collected and the sampler pinched to segment the two portions of blood;

FIG. 3 is a front elevational view of the blood sampler being chilled in an ice bath;

FIG. 4 is a front elevational view of the blood sampler in horizontal position dispensing a sample to a testing machine with a slide clamp;

FIG. 5 is a side elevational view of a type of roller clamp that can be used for strippingly dispensing blood from the sampler; and FIG. 6 is a sectional view of an alternative embodiment of a nonwet filter housing for connecting with a syringe to apply vacuum or pressure to the blood sampler.

DETAILED DESCRIPTION

In FIG. 1, a needle that includes a cannula 1 and a hub 2 is connected through a needle adapter 3 to a flexible tubular reservoir 4. The needle is shown here injected into a patient's artery 5. Arterial blood pressure causes a blood sample 6 to well up in tubular reservoir 4 and expel overriding air 7 through a nonwet filter vent 8 in a filter housing 9. Arterial blood is visually distinguished from venous blood by its fast flow rate and pulsations. FIG. 1 shows a first embodiment of a filter housing 9 which has a generally flat exterior surface 10 that is not adapted to receive a syringe tip. A sliding clamp 11 is loosely fit on tubular reservoir 4.

In FIG. 2, the blood sample has been collected and clamp 11 moved downwardly on tubular reservoir 4 where it pinches the tube shut to segment an air contaminated blood sample portion 12 from a testing portion 13 of the sample. After collecting a sample, it is normal to stick the needle in a rubber stopper or replace the needle with a syringe tip cap (not shown to retain the blood. In FIG. 2, a protector 15 has been placed on the needle, and the rubber stopper could be inside this protector, if desired.

When an arterial blood sample is taken, it is usually tested for the partial pressure of oxygen and carbon dioxide. If the sample taken cannot be tested immediately, it is chilled in an ice bath, such as shown in FIG. 3, to prevent the continual metabolizing of oxygen by the blood sample. The time lag blood sample collection and blood testing might occur where the testing facilities are overloaded with blood samples or there is a considerable distance between the patient and the testing lab.

Once the blood sample is ready for testing, the protector 15 and needle are removed to expose a needle adapter 16 which can connect directly to a blood testing machine 17. Normally, such machine has a small probe that extends inside needle adapter 16 to suck out a measured quantity of the blood sample. In some machines which do not have a vacuum extractor, the blood sample can be slidingly stripped by moving clamp 11 in a forward longitudinal direction along the flexible tubular reservoir 4. As this is done, air is drawn in through the nonwet filter in the filter adapter 9.

The clamp 11, shown schematically in FIG. 4, is a sliding type clamp. An alternate clamp is shown in FIG. 5, which is a roller type clamp with a body 20 and a thumb actuated roller 21 that moves the clamp longitudinally along the flexible tubular reservoir 4. The details of this clamp structure to form this stripping action, as well as the opening and closing action for pinching the reservoir as in FIG. 2, is the subject of a co-pending application, identified at the beginning of this specification.

While the preferred method of collecting a blood sample includes the pinching off of the air contaminated blood sample in a forward chamber of the blood collector, an alternate structure of the filter adapter 25 can have an internally tapered section for connecting to a syringe 26. By pushing a plunger 27 to the left in FIG. 6, a pressure can be created inside of tubular reservoir 4 to force the blood sample into the testing machine 17. However, this has the disadvantage of introducing additional air into the blood sample. Such a syringe attachment can also be used for applying a vacuum by moving plunger 27 to the right of FIG. 6 to aid in collecting a venous blood sample which has reduced pressure.

To aid in mixing the blood sample 13 in FIG. 2 with a dry heparin coating, an optional steel ball 30 can be included in the blood collector and mixing accelerated by shaking or rotating the blood sampler.

The flexible tube permits quick mixing of the dry heparin and blood, as well as remixing any separated plasma and hemoglobin by squeezing or rolling between the operator's hands with a squeezing and ovaling action. It is currently recommended to vigorously roll rigid syringe-type blood samplers 50 times to remix separated plasma and hemoglobin.

In the foregoing description, specific examples have been used to describe the invention. However, it is understood by those skilled in the art that certain modifications can be made to these examples without departing from the spirit and scope of the invention.

I claim:
1. A method of segmenting and dispensing a blood sample to be tested from a flexible tube reservoir containing an air contaminated blood portion comprising the steps of:
  (a) positioning a clamp along a flexible tube reservoir containing a blood sample intermediate the volume of the blood sample to be tested and the contaminated blood portion;
  (b) pinching the clamp to segment the air contaminated blood sample portion from the testing blood sample portion;
  (c) moving the pinched clamp along the flexible tube reservoir to dispense the testing blood sample from the flexible tube reservoir.

* * * * *